(12) United States Patent
Chun (10) Patent No.: US 9,572,946 B2
(45) Date of Patent: Feb. 21, 2017

(54) FACIAL MASK AND ENDOTRACHEAL INTUBATION SYSTEM

(71) Applicant: Dukkyu Chun, Seongnam-shi (KR)

(72) Inventor: Dukkyu Chun, Seongnam-shi (KR)

( * ) Notice: Subject to any disclaimer, the term of this patent is extended or adjusted under 35 U.S.C. 154(b) by 551 days.

(21) Appl. No.: 13/736,950

(22) Filed: Jan. 9, 2013

(65) Prior Publication Data

US 2013/0197303 A1    Aug. 1, 2013

(30) Foreign Application Priority Data

Jan. 30, 2012    (KR) ........................ 10-2012-0010168

(51) Int. Cl.
*A62B 18/08*    (2006.01)
*A62B 18/02*    (2006.01)
(Continued)

(52) U.S. Cl.
CPC .......... *A61M 16/06* (2013.01); *A61B 1/00018* (2013.01); *A61B 1/00052* (2013.01); *A61B 1/267* (2013.01); *A61M 16/0084* (2014.02); *A61B 1/00016* (2013.01); *A61B 1/00048* (2013.01); *A61B 1/05* (2013.01); *A61B 1/0676* (2013.01); *A61M 16/0078* (2013.01); *A61M 16/0488* (2013.01); *A61M 2205/502* (2013.01); *A61M 2205/8206* (2013.01)

(58) Field of Classification Search
CPC .............. A61M 16/00; A61M 16/0084; A61M 16/04–16/0431; A61M 16/0463; A61M 16/0467; A61M 16/0488; A61M 16/06–16/0655; A61M 25/02; A61M 39/00; A61B 1/00; A61B 1/00043–1/00052;A61B 1/00188–1/00197; A61B 1/04–1/053; A61B 1/24; A61B 1/267–1/2676; A61B 5/0033; A61B 5/004
See application file for complete search history.

(56) References Cited

U.S. PATENT DOCUMENTS

| 4,580,556 A | * | 4/1986 | Kondur | .................. A61B 1/267 |
| | | | | 128/206.28 |
| 5,033,818 A | * | 7/1991 | Barr | ........................ B63C 11/12 |
| | | | | 2/428 |

(Continued)

FOREIGN PATENT DOCUMENTS

| JP | 2002-58742 | 2/2002 |
| JP | 2007-509641 | 4/2007 |

(Continued)

OTHER PUBLICATIONS

Author unknown, VBM Medizintechnik GmbH, endoscopy mask, http://www.vbm-medical.de/cms/100-1-endoscopy-mask.html, date unknown("copyright 2006").

(Continued)

*Primary Examiner* — (Jackie) Tan-Uyen T Ho
*Assistant Examiner* — Ned T Heffner (57) ABSTRACT

According to one aspect of this invention, there is provided a medical facial mask having intubation port to insert an endotracheal tube; air ventilation port to perform artificial ventilation during intubation procedure; and a display device to display image of a patient's airway, wherein the image is transmitted from an image acquisition device which is inserted in the patient's airway.

10 Claims, 7 Drawing Sheets

(51) Int. Cl.
*A61M 16/06* (2006.01)
*A61B 1/267* (2006.01)
A61B 1/00 (2006.01)
A61M 16/04 (2006.01)
A61M 16/00 (2006.01)
A61B 1/05 (2006.01)
A61B 1/06 (2006.01)

(56) References Cited

U.S. PATENT DOCUMENTS

| | | | | |
|---|---|---|---|---|
| 5,928,137 | A | * 7/1999 | Green | A61B 1/00052 600/104 |
| 6,631,713 | B1 | * 10/2003 | Christopher | A61M 16/0488 128/200.21 |
| 2007/0286997 | A1 | * 12/2007 | Terao | H01L 51/0035 428/220 |
| 2008/0177146 | A1 | 7/2008 | Chen | |
| 2011/0270038 | A1 | 11/2011 | Jiang et al. | |

FOREIGN PATENT DOCUMENTS

| | | |
|---|---|---|
| JP | 2008528131 A | 7/2008 |
| KR | 10-0894709 | 4/2009 |

OTHER PUBLICATIONS

Author unknown, Life saving medical solutions, Providing the vision for breadth of life, http://www.lsmsusa.com/products.html, date unknown("copyright 2009").

* cited by examiner

FACIAL MASK AND ENDOTRACHEAL INTUBATION SYSTEM

BACKGROUND

When a person's respiration suddenly stops, artificial ventilation may be necessary. One of generally used techniques (practices) is bag mask ventilation, which utilizes Ambu bag and a facial mask. But in order to continue artificial ventilation, endotracheal intubation (or "intubation") is usually necessary. One of common techniques (practices) utilizes direct laryngoscope to visualize patient's airway and insert endotracheal tube ("ETT") into trachea. Another technique (practice) utilizes an ETT with image capture device (image acquisition device) embedded at the tip of the ETT. Medical personnel can easily visualize patient's airway by viewing image (video) displayed on a monitor which is transmitted from the image capture device, such as, for example, a camera.

However, during this intubation process, a patient is in apnea state (i.e., not breathing). And serious brain damage or death could take place if the intubation process is not successfully completed within several minutes.

BRIEF SUMMARY

This summary introduces a selection of concepts in this description which will be described in the Detailed Description in further detail. This summary does not identify key features or essential features of claimed subject matter, and it does not limit the scope of the claimed subject matter.

According to one aspect of this invention, there is provided a medical facial mask comprising: a display device to display an image of a patient's airway, an intubation port to insert an endotracheal tube; and an air ventilation port to perform artificial ventilation during intubation procedure, wherein the image is transmitted from an image acquisition device which is inserted in the patient's airway.

The display device may be detachably installed at the medical facial mask.

The display device may be a flexible display device which is installed at the medical facial mask following the contour of the medical facial mask.

The display device may be a curved panel, and the image displayed on the curved panel may be so amended that the image does not appear to be distorted.

The display device may be installed at the air ventilation port.

The image acquisition device may be inserted in, or installed at the endotracheal tube.

According to one aspect of this invention, there is provided an intubation system comprising: an endotracheal tube; an image acquisition device which is inserted in a patient's airway; and a medical facial mask comprising an intubation port to insert the endotracheal tube, a display device to display an image which is transmitted from the image acquisition device, and an air ventilation port for artificial ventilation.

The display device may be detachably installed at the medical facial mask.

The display device may be a flexible display device which is installed at the medical facial mask following the contour of the medical facial mask.

The display device may be installed at the air ventilation port.

The display device may be a curved panel, and the image displayed on the curved panel may be so amended that the image does not appear to be distorted.

The image acquisition device may be inserted in, or installed at the endotracheal tube.

According to one aspect of this invention, there is provided a medical facial mask which can be utilized for artificial ventilation, comprising a mask body and a face sealing unit, the medical facial mask comprising: intubation port to insert an endotracheal tube; air ventilation port to perform artificial ventilation during intubation procedure; wherein an image acquisition device is inserted in or installed at the endotracheal tube, and the intubation port is movably attached to the mask body.

The intubation port may be connected to the mask body by elastic material.

BRIEF DESCRIPTION OF THE SEVERAL VIEWS OF THE DRAWINGS

The invention will be more fully understood when reference is had to the following detailed description of the prior arts and preferred embodiment of the invention that accompany drawings, in which.

DETAILED DESCRIPTION OF THE INVENTION

This invention can have many variations and embodiments. Some of the embodiments will be explained with some figures, as below.

Figure 1:
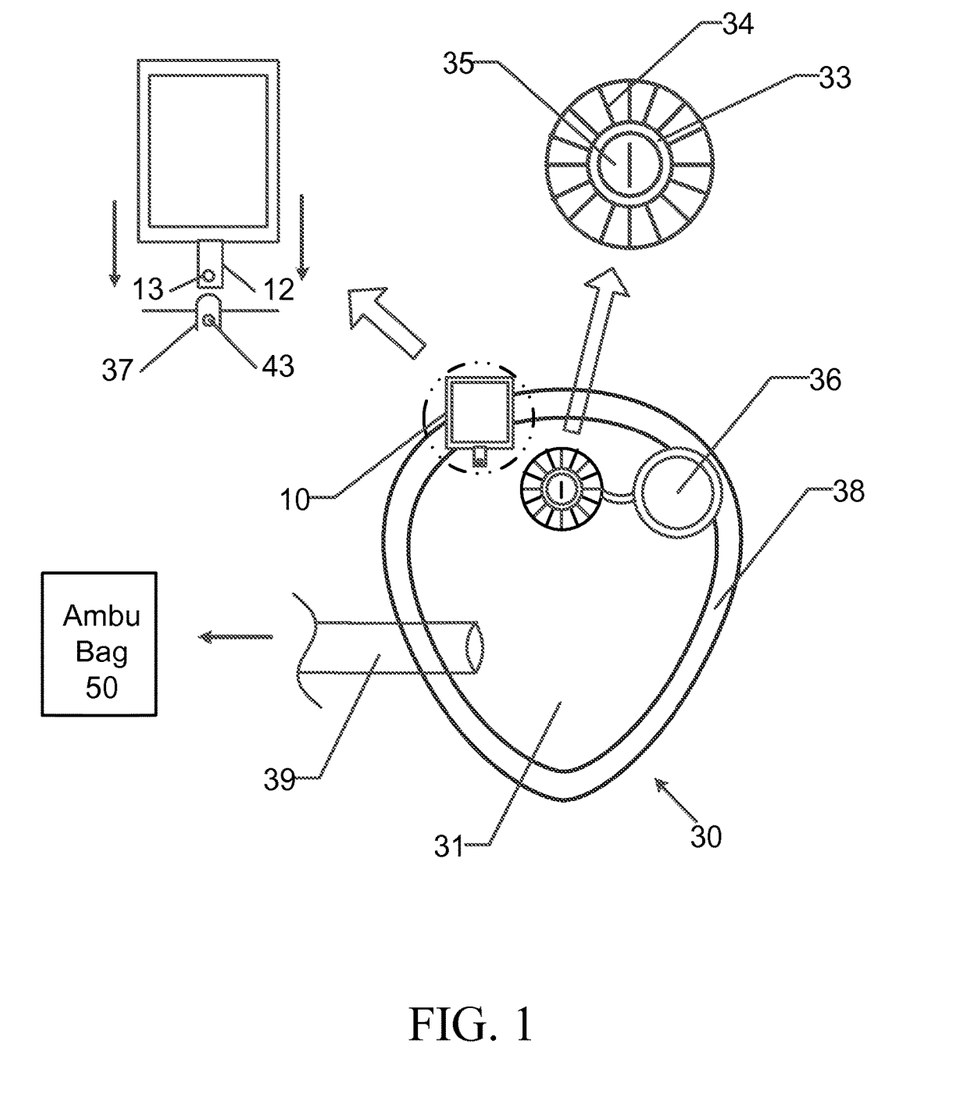
FIG. 1 illustrates a view from above of a facial mask according to one embodiment of this invention.
Figure 2:
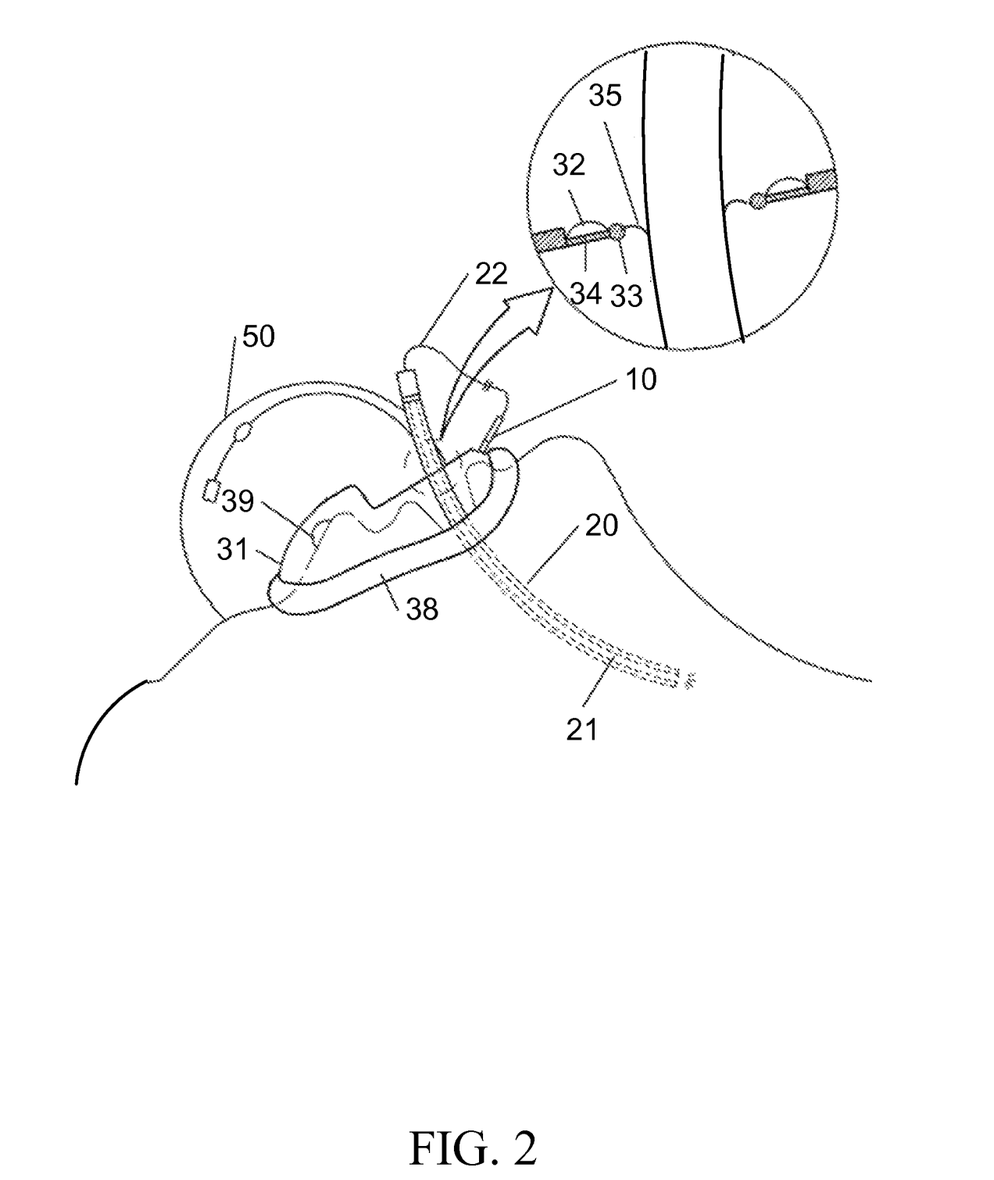
FIG. 2 illustrates a side view of a facial mask and endotracheal intubation system, according to one embodiment of this invention.

A facial mask and endotracheal intubation system according to one embodiment of this invention will be described with reference to FIG. 1 and FIG. 2.

The endotracheal intubation system of this embodiment comprises a medical facial mask 30 (hereinafter referred as "facial mask") by which artificial ventilation can be perfumed, ambu bag 50, endotracheal tube 20 and display device 10. A device which can acquire or capture image of patient's body ("image capture device", or "image acquisition device"), such as, for example, a tracheoscope 21 is inserted and installed in the endotracheal tube 20. More particularly, at the front end of endotracheal tube 20, a camera and a light source are positioned and continuously capturing image of patient's airway, such as, for example, laryngo-pharnx or entrance of trachea. The captured image is transmitted to the display device 10 in real time by connection cable 22, and a medical personnel checks the image (video) displayed. Because the image capture device is continuously capturing airway image, a medical personnel can view the image on a display device as a video. The captured image may be transmitted to the display device 10 by a cable as illustrated in FIG. 2, or it may be transmitted by wireless means. For wireless connection, the image capture device may be equipped with or connected to a wireless transmission means, and the display device 10 may be equipped with or connected to a wireless receiver means. Techniques regarding tracheoscope (or image capture device similar to it), endotracheal tube in which the tracheoscope may be inserted or installed, and monitor connected with the tracheoscope are well known to a person of ordinary skill in the art, and will not be described in further detail.

According to this embodiment, the facial mask 30 comprises face sealing unit 38 and mask body 31. The mask body 31 may be made of solid plastic material. The face sealing unit 38 is made of flexible material to fit in to various shapes of patients' faces, and provide air-tight sealing when the facial mask 30 is applied to the patient's face. As illustrated in FIG. 2, height of the mask body 31 may be designed and manufactured to be smaller around patient's mouth orifice than other areas, so that endotracheal intubation through the facial mask may be performed easily. The facial mask 30 comprises intubation port (or entrance) 33 for endotracheal intubation, as well as air ventilation port 39 for artificial ventilation. A display device 10 to display image which is transmitted or delivered from image capture device (inserted in the endotracheal tube 20) is installed at the facial mask 30. A monitor is utilized as an example of the display device in this embodiment. The display device may be (semi) permanently installed at the facial mask 30 during manufacturing process of the facial mask 30. Or the display device 10 may be temporarily installed (attached) at the facial mask when in use, and be removed (detached) when not in use. In this embodiment, the display device 10 is temporarily installed on facial mask 30. The facial mask 30 has "monitor anchoring shaft" 37 to install and support the display device 10.

Next, intubation port 33 according to this embodiment will be described. The intubation port 33 is a port or entrance through which an endotracheal tube 20 is inserted. The intubation port 33 may have ring shape, and margin of the intubation port 33 may be made of plastic material, for instance. Inner area of the intubation port 33 has sealing part 35, which is a flexible and distensible membrane or diaphragm. The sealing part 35 may be made of silicone or silastic, for example. The endotracheal tube 20 is inserted through a slit on the sealing part 35. The sealing part 35 allows insertion of endotracheal tube 20 while maintaining air-tight sealing. In order to provide sufficient mobility during endotracheal intubation, the intubation port 33 is coupled (connected) to the mask body 31 by "movable part", such as, for example, elastic material. In other words, the intubation port 33 is movably attached to the mask body 31. More particularly, the intubation port 33 is attached to and supported by the mask body 31 via elastic material such as, for example, elastic fiber 34. As a result, endotracheal tube 20 which is inserted through the movable intubation port 33 can have sufficient mobility to efficiently perform endotracheal intubation through the facial mask 30. Regarding elastic fiber 34, elasticity and/or length of the elastic fiber 34 of all positions (such as, for example, up, down, right and left) don't need to be made identical to one another. It is possible to allow more up and down movement, while allowing smaller right and left movement, for instance. Above the elastic fibers, elastic fiber cover 32 is installed to prevent air leakage through the elastic fibers. The elastic fiber cover 32 may be made of flexible material. Within a circle of FIG. 2, cross sections of the intubation port 33, endotracheal tube 20 and related structures are illustrated in detail. There could be small gap (space) between the sealing part 35 and the endotracheal tube 20 which can be ignored clinically (not illustrated).

A display device 10 such as, for example, a monitor which is installed at facial mask 30, according to this embodiment will be described. The monitor is installed at the facial mask 30 to display image transmitted from an image capture device such as, for example, a tracheoscope which is inserted in an endotracheal tube 20. The facial mask 30 has monitor anchoring shaft 37, which has protrusion 43. The monitor has a support shaft 12, which has a hole 13. A user can install the monitor to the facial mask 30 manually by inserting the support shaft 12 of the monitor to the monitor anchoring shaft 37 of the facial mask 30, which are firmly joined together by interlocking of the protrusion 43 and the hole 13. It is also possible to utilize any other techniques, such as, for example, a screw, to install the monitor at the facial mask 30. The monitor may have control unit, battery unit, receiver unit, switch unit etc, which are well known to a person of ordinary skill in the art, and will not be described further.

Next, intubation procedure using the facial mask and intubation system according to this embodiment, will be described. If an emergency situation requiring CPR (cardiopulmonary resuscitation) takes place, or when induction of general anesthesia is performed, facial mask 30 is applied to a patient's face. Then ambu bag 50 is connected to air ventilation port 39 of the facial mask 30, and bag mask ventilation is started. Air ventilation port 39 may be connected to other devices, such as, for example, mechanical ventilation circuit, if available. If endotracheal intubation is determined, an endotracheal tube 20 with image capture device is prepared. Image capture device, such as, for example, a tracheoscope 21 is pre-installed or inserted within the endotracheal tube 20. A sealing cap may be placed at upper tip of the endotracheal tube 20 in order to seal the space between the tracheoscope 21 and the endotracheal tube 20. Then a monitor connected with the tracheoscope 21 is installed and fixed at monitor anchoring shaft 37 of facial mask 30. Then, intubation port 33 is opened by removing a cover 36 of facial mask 30. And endotracheal tube 20 with tracheoscope 21, is grabbed by a medical personnel's hand and inserted into patient's mouth through the intubation port 33. Then the endotracheal tube 20 is further inserted into patient's larynx and entrance of tracheal (vocal cord), while image (video) displayed on the monitor is viewed. During this procedure, artificial ventilation is continuously performed by bag mask ventilation. If it is confirmed that current position of a tip of the endotracheal tube 20 is at the entrance of trachea (vocal cord), by viewing image displayed on the monitor, the endotracheal tube 20 is further advanced and inserted into the trachea. Then cuff is expanded by air infusion, and the endotracheal tube 20 is fixed in the trachea.

Then tracheoscope 21 is removed from the endotracheal tube 20, and monitor is removed from the monitor anchoring shaft 37. And facial mask 30 is removed carefully from endotracheal tube 20. It is also possible to leave tracheoscope 21 within the endotracheal tube 20 for continuous monitoring of patient's airway, if the tracheoscope 21 does not hinder patient's ventilation.

As described above, according to one aspect of this invention, intubation port 33 for endotracheal intubation is installed at a facial mask 30 by which artificial ventilation can be performed. The intubation port 33 itself is movably connected to mask body via movable part such as, for example, elastic material. The movable part is distensible and resilient. The intubation port 33 itself is movable while preserving air tight sealing around endotracheal tube 20. Because the intubation port 33 is movable (i.e., positional coordinate of intubation port 33 itself can be changed), an endotracheal tube 20 inserted through the intubation port 33 is also movable (up, down, right or left etc.). "Up" or "down" means a direction toward a patient's chin or head, respectively. Thus, intubation procedure through facial mask may be performed by simply holding an endotracheal tube and directly controlling position or movement of it by hand. It does not require remote controlled endoscopy to control position or movement of tip of endotracheal tube 20, the skill of which takes time and efforts to learn. Utilizing the facial mask and intubation system of this embodiment, a medical personnel can easily and effectively perform endotracheal intubation while continuously performing artificial ventilation. In other words, because air supply to a patient is continued by mask ventilation during endotracheal intubation, this procedure may prevent liabilities due to oxygen dificiency such as, for example, brain damage, or death, even if it should take extra time to intubate endotracheal tube in unexpected problematic situations. As stated above, complex endoscopy procedure is not necessary.

In many emergency situations, it may be difficult to find a place or instrument to install or fix a monitor (or other display device) to display image transmitted from image capturing device installed at endotracheal tube. It may be even more difficult if the emergency situation suddenly takes place at unexpected places such as, for example, in a classroom, inside a train etc. However, in this embodiment, the display device is fixed at a facial mask, which is already in position on a patient's face to perform bag mask ventilation and readily available. As a result, when emergency situation takes place, an image of patient's airway can be obtained quickly and stably without wasting time to find an appropriate place or instrument to install the display device.

This embodiment also has some more advantages. The facial mask is not a moving device or instrument, but (basically) fixed on a patient's face. As a result, a display device fixed or installed at the facial mask can provide stable image of patient's airway to a medical personnel during intubation. It should be noted that the display device on a facial mask is automatically situated close to a medical personnel during intubation, compared with other situations, where a patient's airway image is displayed on a laptop screen, for instance, which may be positioned far from medical personnel. Because the display device is near to the medical personnel, the display device doesn't need to be made large and still the medical personnel can get clear image of the patient's airway and information regarding current position of a tip of the endotracheal tube. Furthermore, because the display device 10 is positioned right on a patient's face, a medical personnel can continuously monitor the patient's condition, such as, for example, facial appearance or seizure, by viewing the patient while performing endotracheal intubation, during which continuous air ventilation is also performed.

According to conventional technology, when a display device, such as, but not limited to, a monitor is to be installed suddenly in unexpected emergency situations, there is no guarantee that the monitor will be placed in an efficient position for a medical personnel to view during intubation. However, according to this embodiment, the monitor is installed on a certain predetermined position on the facial mask, which is a predetermined efficient position for a medical personnel to view during intubation. It is more advantageous in human ergonomics' point of view as well as efficiency of intubation, to look at a monitor installed at predetermined efficient position, compared with a situation wherein a monitor is abruptly installed at nearby random place and requires a medical personnel to rotate his/her neck to get a view of it, for instance.

As a result, according to this embodiment, medical personnel can perform endotracheal intubation safely and effectively when emergency situation takes place even in certain places other than well prepared hospital settings, such as, for example, ICU (intensive care unit).

Figure 3:
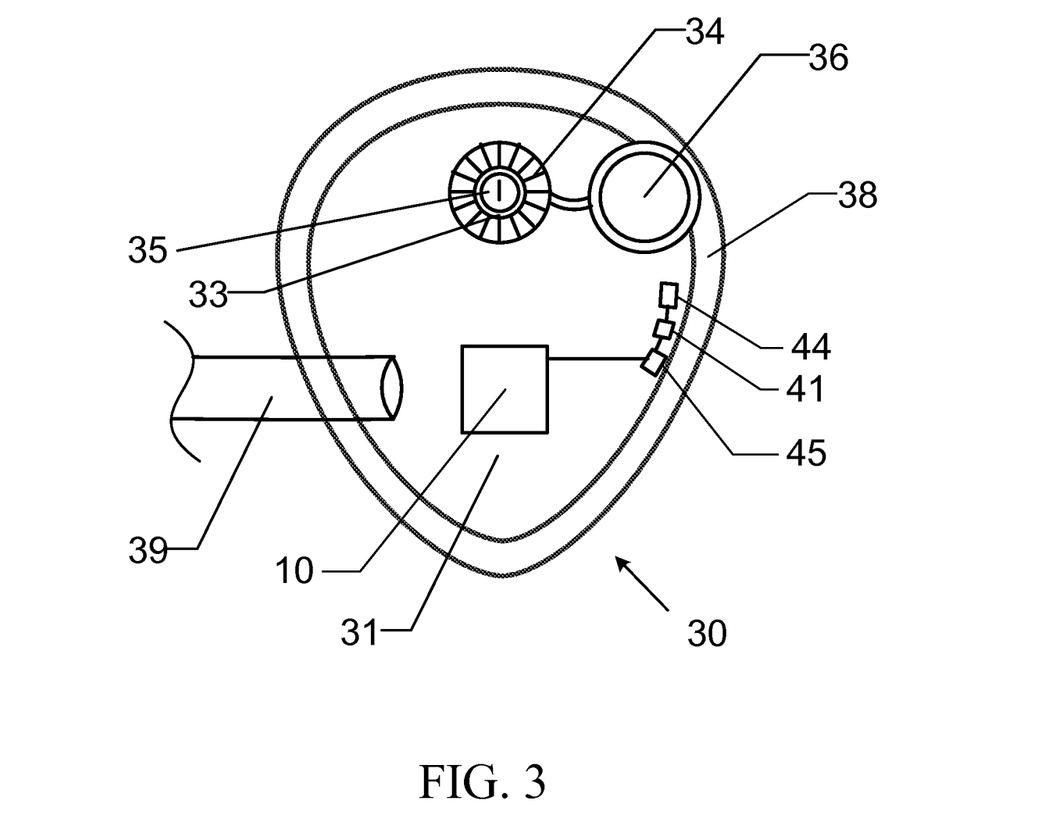
FIG. 3 illustrates a view from above of a facial mask according to another embodiment of this invention.
Figure 4:
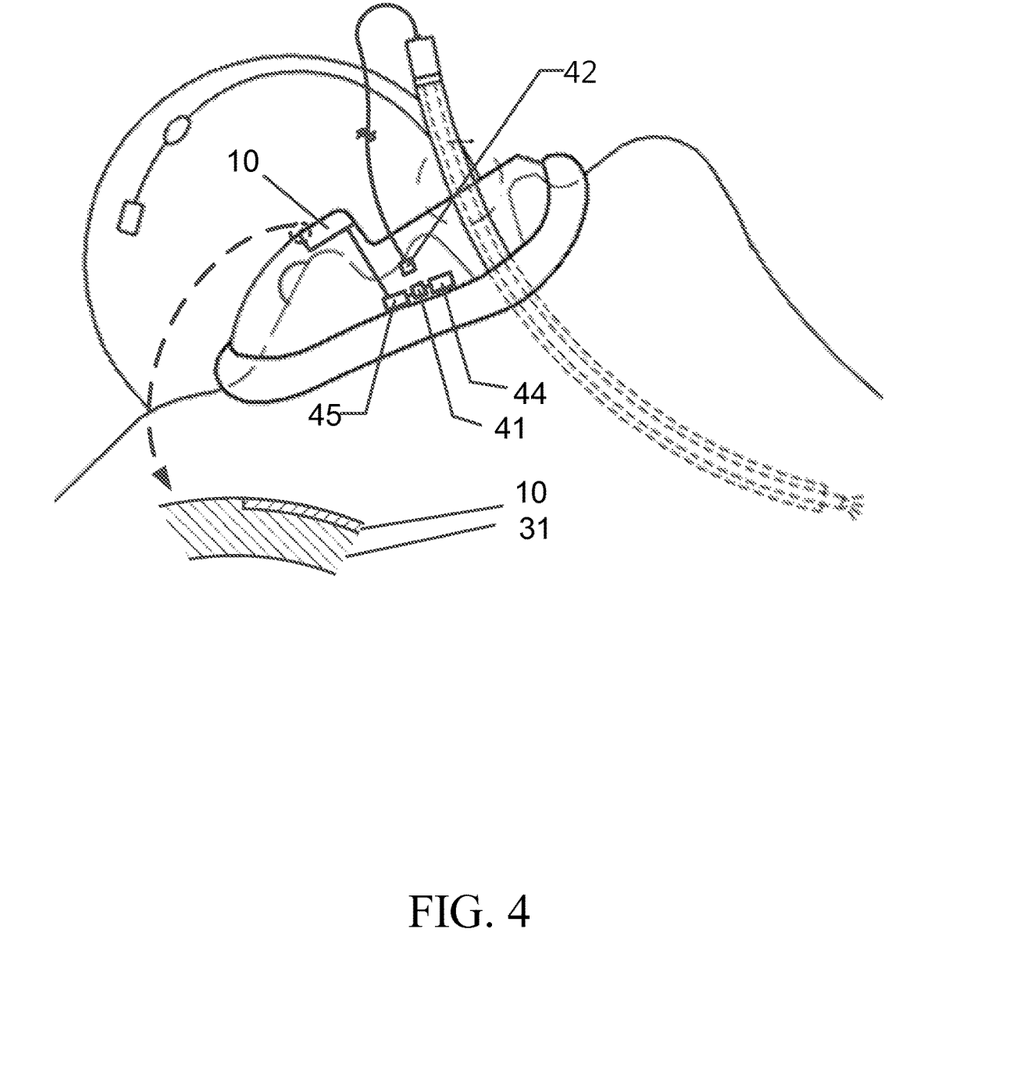
FIG. 4 illustrates a side view of a facial mask and endotracheal intubation, according to another embodiment of this invention.

Next, a facial mask and intubation system according to another embodiment of this invention are described. In this embodiment also, a display device to display image of patient's airway is installed at facial mask 30. But the display device is not temporarily attached to and removed from the facial mask. It is embedded, or built in mask body 31 of facial mask 30. In this embodiment, certain elements such as, for example, control unit, receiver unit and power supply unit are described to be separate from the display device. The facial mask comprises display device 10, receiver unit 41, control unit 45 and power supply unit 44. In this embodiment, flexible display such as, for example, flexible OLED (organic light emitting diode) display is utilized as a display device 10. Flexible display can be made with flexible substrate, and be made thin, light and flexible. A flexible display and OLED display are already commercialized technology and will not be described in further detail. The flexible display is installed at the facial mask 30 according to (following) the surface shape of the mask body 31. More particularly, the flexible display is manufactured in a shape which corresponds to the shape (contour) of the mask body surface. Then the flexible display is tightly attached to the mask body 31, according to (following) the surface shape of the mask body 31. The flexible display may be attached to outer surface or inner surface of the mask body 31. The flexible display may also be attached to, or inserted at internal layer of the mask body 31 (within mask body's layer).

In this embodiment, image or picture data captured (acquired) by the image capture device such as, for example, a tracheoscope is delivered to transmitter unit 42 and then transmitted to the receiver unit 41 of facial mask, by coupling of the transmitter unit 42 and the receiver unit 41. The transmitted image is delivered to control unit 45 and processed to be picture data suitable for being displayed on the flexible display. Then the image is transmitted to and displayed on the flexible display. In order to supply power for electrical operations on facial mask 30, power supply unit 44 is installed on the facial mask. It is also possible to get power from outside of the facial mask 30. The control unit 45 may also be installed at equipment(s) other than facial mask 30, such as, for example, a tracheoscope.

In this embodiment, a flexible display using OLED display was not only built in the facial mask 30 but was embedded in the layer of the mask body 31. The flexible display has become one of many elements which constitute the mask body 31. The flexible display functions as a display device to display patient's airway image during intubation, but functions as a mask layer to protect and seal a patient's face when intubation is not being performed. It is also possible to utilize a transparent OLED as the flexible display, to allow visualization of patient's face through the transparent OLED when intubation is not being performed.

According to this embodiment, when emergency situation takes place, an image of patient's airway can be obtained quickly and stably, by just connecting the transmitter unit 42 (of the image capture device) and receiver unit 41 (of facial mask 30). In this way, there is no need to find a display device and install the display device, not to mention the fact that there is no need to waste time to find an appropriate place or instrument to install the display device. This embodiment also has advantage in that it can save space for installing display device 10. Because the display device 10 is tightly attached to mask body 31 according to the surface shape of the mask body 31, it does not require separate space for installing the display device 10. It should also be noted that there is no need for separate device to accommodate or fix the display device such as, for example, a frame, shaft, or holder etc. As a result, hardware resources can be saved and weight of the facial mask 30 with built-in display device can be decreased. Other details can be implemented in the same or equivalent way as described in the above embodiment, and will not be repeated.

Figure 5:
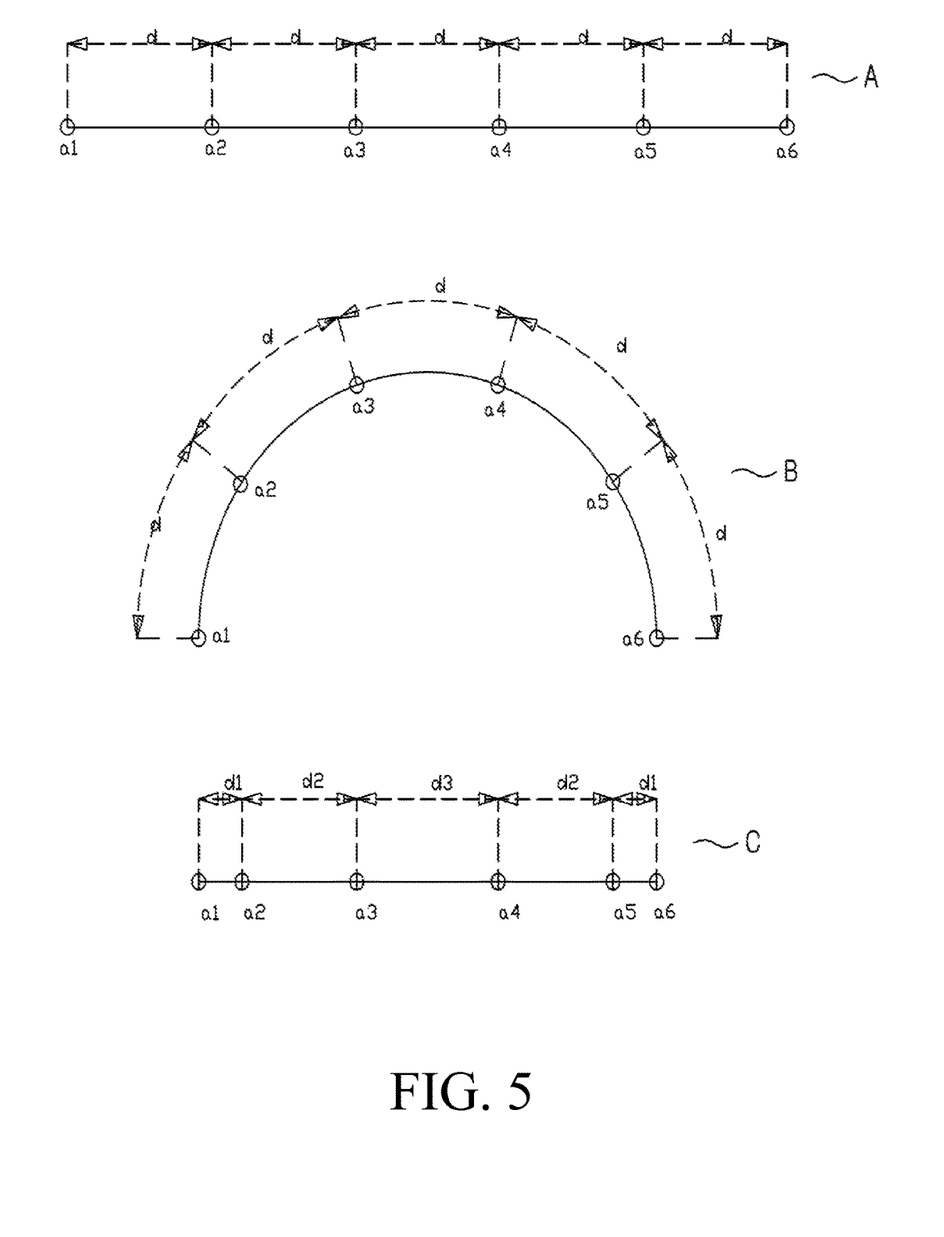
FIG. 5 is an illustration to explain image distortion on a curved display panel, according to another embodiment of this invention.
Figure 6:
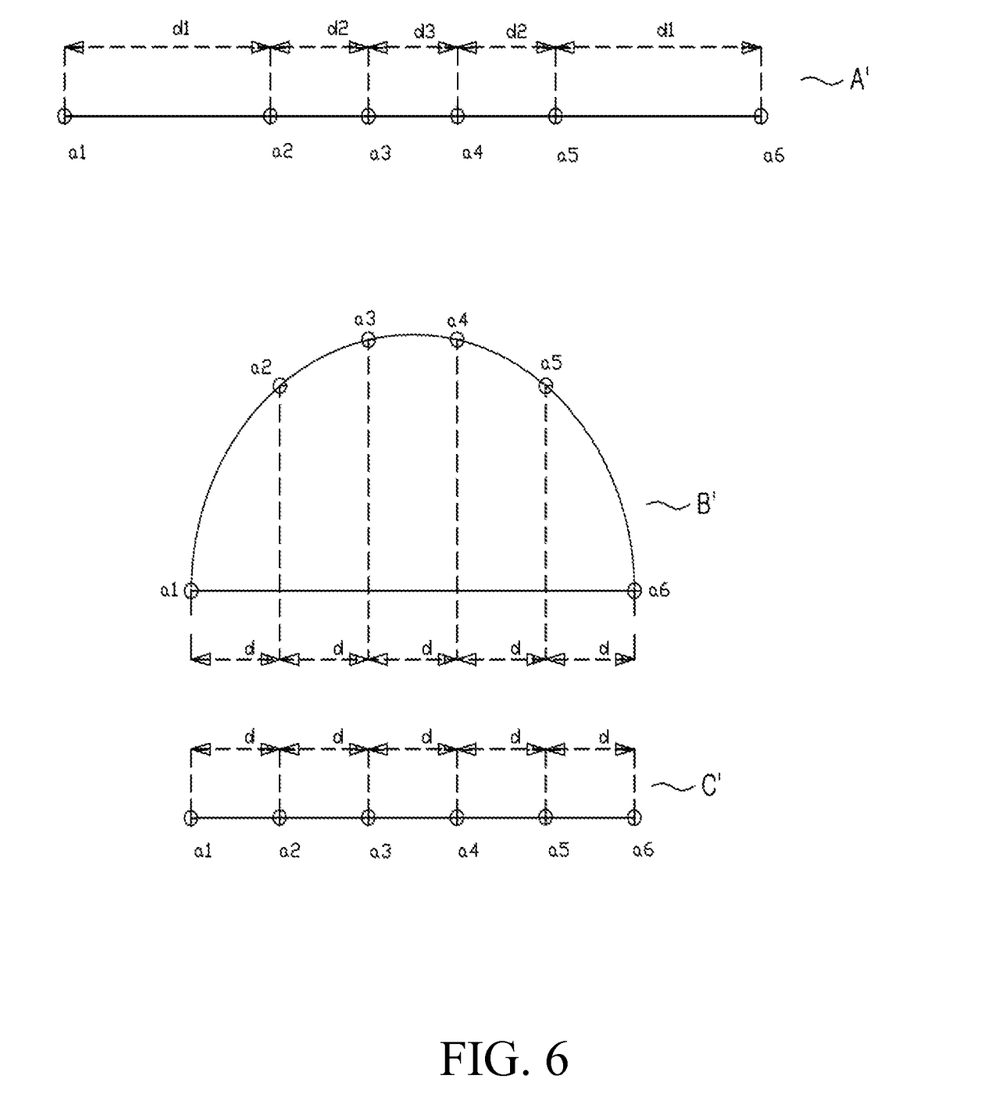
FIG. 6 is an illustration to explain correction (amendment) of image distortion on a curved display panel, according to another embodiment of this invention.

Next, image distortion phenomenon on a curved display panel and amending process to solve this problem, according to one embodiment of this invention will be described. In this embodiment, display device 10 is a curved display panel bent according to (following) shape of mask body. And the amending process is intended to amend (correct) picture or image on the curved display panel so that the image can be viewed without distortion. The amending process may be performed by control unit 45 installed at the facial mask 30.

FIG. 5 illustrates the image distortion phenomenon on a curved display panel of this embodiment. In general, display devices have many pixels which have each coordinate along horizontal and vertical axis on two dimensional plane. "A" of FIG. 5 illustrates that an image contains six points with same intervals on an arbitrary horizontal axis on a flat display panel. And "B" illustrates a picture when the display panel is bend or curved. "C" illustrates a picture how the six points displayed on a curved display panel will appear to a viewer. As in this example ("C"), if the display panel has convex shape, the six points will not appear to be distributed with same intervals. The intervals among points on central area of the curved display panel will appear to be larger than intervals on peripheral areas of the curved display panel. Same principle may apply to points along a vertical axis as in horizontal axis.

FIG. 6 illustrates how to amend an image on a curved display panel so that the image does not appear to be distorted to a viewer, according to this embodiment. "C'" of FIG. 6 illustrates an image which is intended to appear to a viewer. The image contains six points along horizontal axis distributed with same intervals. With reference to "B'" of FIG. 6, a curved line is drawn on a virtual space on a computer monitor, following actual curvature of the curved display panel. Then six points are positioned on the curved line. The positions are intersection points with the curved line and vertical lines drawn from each point on C'. Then the curved line (B') is straightened to be a straight line as in A' by computer software. The six points on the straight line (A') are not distributed at same intervals. The intervals among points on central area of the curved display panel are smaller than intervals on peripheral areas of the curved display panel. If a command to display points as in A' is transmitted to a convex curved panel as in B', the points would appear to a viewer as in C', i.e., without distortion due to panel curvature. Same principle may apply to points along vertical axis as those along horizontal axis.

If this amending process is performed many times (as many as number of pixels along an axis) along horizontal axis and vertical axis, an image displayed on a curved display panel would appear to be a picture without distortion to a viewer, as on a flat display panel.

Figure 7:
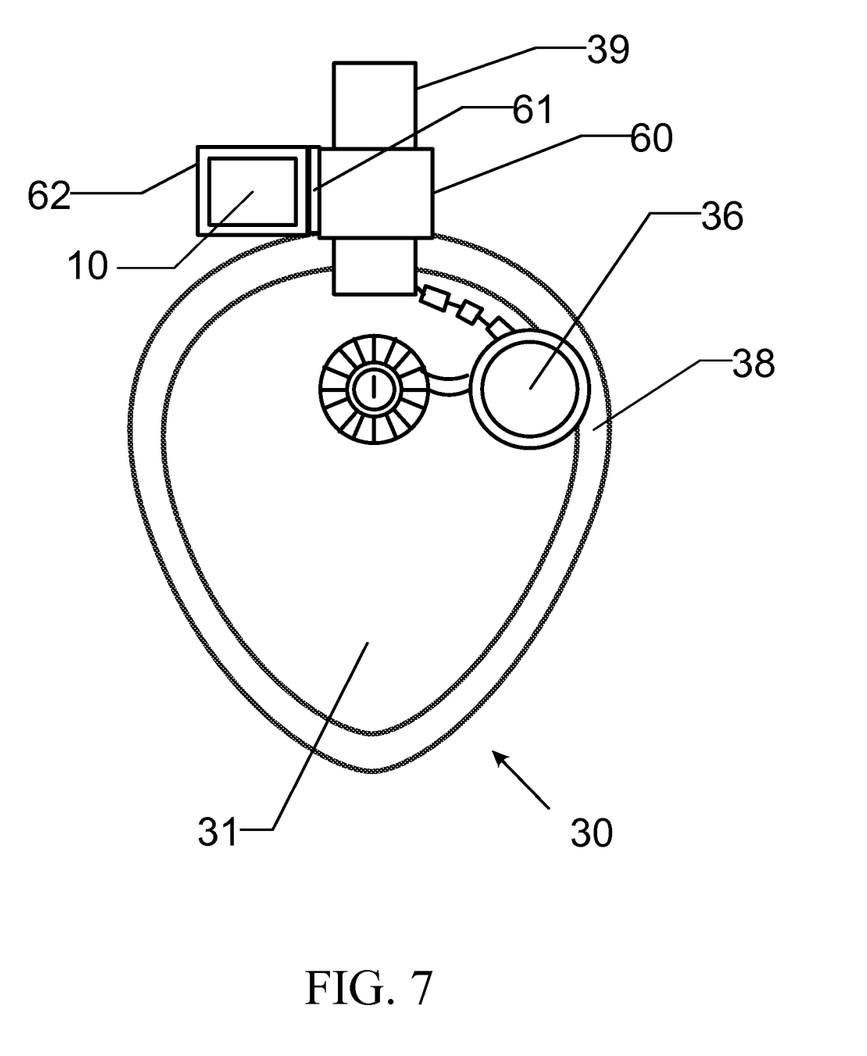
FIG. 7 illustrates an oblique view of a facial mask according to another embodiment of this invention.

With reference to FIG. 7, another embodiment of this invention is described. A flexible display is utilized as a display device 10 to display image of patient's airway (transmitted from image capture device inserted in endotracheal tube 20). The display device 10 is installed at facial mask 30, but not at mask body 31, but at air ventilation port 39. The air ventilation port 39 is positioned along vertical axis of facial mask 30. The air ventilation port 39 basically has circular cross sectional area. Some portion of the air ventilation port 39 is surrounded by "monitor attachment pillar" 60 which has oval cross sectional area. With regard to the oval cross sectional area, length of horizontal axis is longer than vertical axis (not illustrated). At the front of the monitor attachment pillar 60, "cover of attachment pillar" 62 is installed, which can be opened by rotation around a hinge 61. The display device 10 to display patient's airway image is installed at inner side of the cover of attachment pillar 62, which can be viewed by medical personnel when the cover of attachment pillar 62 is opened. More particularly, a thin flexible display, such as, for example, flexible OLED display is tightly attached to the inner side of the cover of attachment pillar 62, according to (following) the shape of the inner side surface of the cover. The display device 10 is a curved display panel, with concave shape. A technique (process) of amending image distortion phenomenon on curved display panel was already described above. In this embodiment, the display device 10 has concave shape instead of convex shape. The amending process can be performed in a similar way but in opposite way. As a result, a medical personnel can easily get a view of patient's airway displayed on the display device 10 pre-installed at the air ventilation port 39. Other details can be implemented in the same or equivalent ways as in the embodiments described above, and will not be repeated.

According to one embodiment, the display device 10 may be installed on outer surface (frontal area) of the monitor attachment pillar 60, which may be covered by a protection film.

The figures referred above are not made according to exact scales. In the embodiments described above, a display device to display patient's airway image was installed at a facial mask 30 wherein intubation port 33 is connected to mask body by a movable unit (part). But the display device 10 may be installed at other facial masks. The image sent from an image capture (acquisition) device may be transmitted to display device 10 by various transmission means, such as, for example, electrical wire means or wireless transmission means.

In the embodiments described above, some devices or units, such as, for example, receiver unit, power supply unit, and control unit were installed on facial mask 30, but they may be installed at other instrument or place.

In the embodiments described above, an image capture device (image acquisition device) was inserted in and installed at endotracheal tube 20. But the image capture device may be installed at other instrument or place which can be inserted in a patient's airway.

The expressions such as "a" or "an" to describe any element in this description or claims do not necessarily mean that there is only one of the element. The expressions using plural nouns to describe any element(s) in this description or claims do not necessarily means that there are always multiple elements.

The invention is not restricted to the particular details listed herein. Indeed, those skilled in the art will appreciate that many other variations from the foregoing description and drawings may be made within the scope of the present invention.

The invention claimed is:

1. A medical facial mask comprising:
a display device to display an image of a patient's airway;
an intubation port to insert an endotracheal tube; and
an air ventilation port to perform artificial ventilation during intubation procedure,
wherein the image is transmitted from an image acquisition device which is inserted in the patient's airway, and the display device can be stably fixated at a structure of the facial mask.

2. The medical facial mask as set forth in claim 1, wherein the display device is installed at the air ventilation port.

3. The medical facial mask as set forth in claim 1, wherein the image acquisition device is inserted in, or installed at the endotracheal tube.

4. The medical facial mask as set forth in claim 1, wherein the display device is a flexible display device which is installed at the medical facial mask following the contour of the medical facial mask.

5. The medical facial mask as set forth in claim 4, wherein the display device is a curved panel, and an image displayed on the curved panel is so amended that the image does not appear to be distorted.

6. An intubation system comprising:
an endotracheal tube;
an image acquisition device which is inserted in a patient's airway; and
a medical facial mask comprising a display device to display an image which is transmitted from the image acquisition device, an intubation port to insert the endotracheal tube, and an air ventilation port for artificial ventilation, wherein the display device can be stably fixated at a structure of the facial mask.

7. The intubation system as set forth in claim 6, wherein the display device is a flexible display device which is installed at the medical facial mask following the contour of the medical facial mask.

8. The intubation system as set forth in claim 6, wherein the image acquisition device is inserted in, or installed at the endotracheal tube.

9. The intubation system as set forth in claim 6, wherein the display device is installed at the air ventilation port.

10. The intubation system as set forth in claim 7, wherein the display device is a curved panel, and an image displayed on the curved panel is so amended that the image does not appear to be distorted.

* * * * *